(12) United States Patent
Takei

(10) Patent No.: US 11,311,307 B2
(45) Date of Patent: Apr. 26, 2022

(54) MANUFACTURING METHOD OF A GRASPING DEVICE AND TREATMENT INSTRUMENT

(71) Applicant: OLYMPUS CORPORATION, Hachioji (JP)

(72) Inventor: Yusuke Takei, Hino (JP)

(73) Assignee: OLYMPUS CORPORATION, Tokyo (JP)

( * ) Notice: Subject to any disclaimer, the term of this patent is extended or adjusted under 35 U.S.C. 154(b) by 431 days.

(21) Appl. No.: 16/510,221

(22) Filed: Jul. 12, 2019

(65) Prior Publication Data
US 2019/0328414 A1    Oct. 31, 2019

Related U.S. Application Data

(63) Continuation of application No. PCT/JP2017/000848, filed on Jan. 12, 2017.

(51) Int. Cl.
*A61B 17/29*    (2006.01)
*A61B 17/00*    (2006.01)
(Continued)

(52) U.S. Cl.
CPC ............ *A61B 17/29* (2013.01); *A61B 18/085* (2013.01); *A61B 18/1447* (2013.01);
(Continued)

(58) Field of Classification Search
CPC ............ A61B 17/29; A61B 2017/2936; A61B 2017/2939; A61B 2017/2944;
(Continued)

(56) References Cited

U.S. PATENT DOCUMENTS

| 3,459,187 A | 8/1969 | Pallotta |
| 4,669,471 A | 6/1987 | Hayashi |

(Continued)

FOREIGN PATENT DOCUMENTS

| JP | S60-222047 A | 11/1985 |
| JP | H10-211208 A | 8/1998 |

(Continued)

OTHER PUBLICATIONS

Apr. 4, 2017 International Search Report issued in International Application No. PCT/JP2017/000848.

(Continued)

*Primary Examiner* — Majid Jamialahmadi
(74) *Attorney, Agent, or Firm* — Oliff PLC

(57) ABSTRACT

In a manufacturing of a grasping device that is openable and closable and includes a first jaw having a first hole and a second jaw having a second hole larger than the first hole, the first jaw is arranged in between protruding portions of the second jaw. The second hole is located outside the first hole in a width direction of the grasping device, and a cross-sectional area of the second hole is larger than the first hole. A pin member is inserted through both the first hole and the second hole. The positions of the first jaw and the pin member are adjusted relative to the second jaw to predetermined positions. The pin member is fixed to the second jaw upon positioning the first jaw and the second jaw at the predetermined positions.

8 Claims, 10 Drawing Sheets

(51) Int. Cl.
    *A61B 18/08* (2006.01)
    *A61B 18/14* (2006.01)
(52) U.S. Cl.
    CPC .............. *A61B 2017/00526* (2013.01); *A61B 2017/2939* (2013.01); *A61B 2017/2947* (2013.01)
(58) Field of Classification Search
    CPC .... A61B 2017/2947; A61B 2017/2926; A61B 2017/00526; A61B 18/085; A61B 18/1445; A61B 18/1447
    See application file for complete search history.

(56) References Cited

U.S. PATENT DOCUMENTS

| | | | |
|---|---|---|---|
| 5,649,958 | A | 7/1997 | Grimm et al. |
| 6,083,240 | A | 7/2000 | Ouchi |
| 6,406,475 | B1 | 6/2002 | Wenzler et al. |
| 2004/0073208 | A1 | 4/2004 | Sutter |
| 2013/0296922 | A1* | 11/2013 | Allen, IV ........... A61B 18/1445 606/205 |

FOREIGN PATENT DOCUMENTS

| | | |
|---|---|---|
| JP | 2000-051227 A | 2/2000 |
| WO | 2016/067950 A1 | 5/2016 |

OTHER PUBLICATIONS

Jul. 25, 2019 English translation of the IPRP issued in International Application No. PCT/JP2017/000848.

\* cited by examiner

MANUFACTURING METHOD OF A GRASPING DEVICE AND TREATMENT INSTRUMENT

CROSS-REFERENCE TO RELATED APPLICATIONS

This is a Continuation Application of PCT Application No. PCT/JP2017/000848, filed Jan. 12, 2017, the entire contents of which are incorporated herein by reference.

BACKGROUND

1. Field of the Invention

The exemplary embodiments relate to a manufacturing method of a grasping device that is openable and closable between a pair of jaws and relates to a treatment instrument including this grasping device.

2. Description of the Related Art

A treatment instrument including a grasping unit treats a treatment target by grasping the treatment target between the jaws and applying treatment energy to the grasped treatment target.

SUMMARY

According to one aspect of the exemplary embodiments, there is a manufacturing method of a grasping unit that is openable and closable between a first jaw having a first hole and a second jaw having a second hole larger than the first hole. The method includes: inserting a pin member into the first hole and the second hole in a state where the second hole is located outside the first hole in a width direction of the grasping unit, the pin member defining a rotation axis of the first jaw and/or the second jaw in an open and close motion between the first jaw and the second jaw; adjusting relative positions of the first jaw and the second jaw to predetermined positions in a state where the pin member is inserted into the first hole and the second hole; and joining the pin member to the second jaw in a state where the first jaw and the second jaw are adjusted to the predetermined positions.

According to another aspect of the exemplary embodiments, a treatment instrument includes; an elongated member having a longitudinal axis; an end effector provided on a distal side of the elongated member; and a housing to which a proximal side of the elongated member is connected. The end effector includes: a first jaw having a first hole; a second jaw having a second hole located outside the first hole in a width direction of the end effector, the second hole being larger than the first hole; and a pin member inserted into the first hole and the second hole and defining a rotation axis of the first jaw and/or the second jaw in an open and close motion between the first jaw and the second jaw.

Advantages of the exemplary embodiments will be set forth in the description which follows, and in part will be obvious from the description, or may be learned by practice of the exemplary embodiments. The advantages of the exemplary embodiments may be realized and obtained by means of the instrumentalities and combinations particularly pointed out hereinafter.

BRIEF DESCRIPTION OF THE SEVERAL VIEWS OF THE DRAWINGS

The accompanying drawings, which are incorporated in and constitute a part of the specification, illustrate exemplary embodiments, and together with the general description given above and the detailed description of the embodiments given below, serve to explain the principles of the exemplary embodiments.

DETAILED DESCRIPTION

First Embodiment

Figure 1:
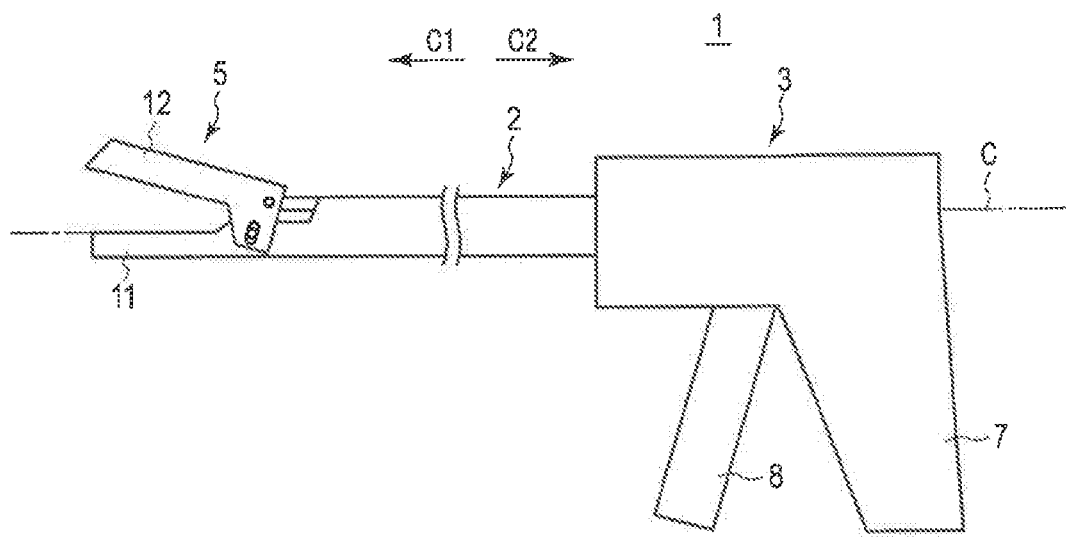
FIG. 1 is a schematic view showing an example of a treatment instrument manufactured by a manufacturing method according to a first embodiment.

The first embodiment will be described with reference to FIGS. 1 to 12. FIG. 1 is a schematic view showing an example of a treatment instrument 1 manufactured by a manufacturing method according to the present embodiment. As shown in FIG. 1, the treatment instrument 1 includes a shaft 2, a housing 3, and a grasping unit (end effector) 5. The shaft 2 has a longitudinal axis C as a central axis and extends along the longitudinal axis C. One side in the direction along the longitudinal axis C is referred to as a distal side (arrow C1 side), and the side opposite to the distal side is referred to as the proximal side (arrow C2 side). The housing 3 is connected to the proximal side of the shaft 2. Furthermore, the grasping unit 5 is provided in the distal portion of the shaft 2.

The housing 3 is provided with a grip 7, and a handle 8 is rotatably mounted to the housing 3. The handle 8 pivots relative to the housing 3 such that the handle 8 is opened or closed relative to the grip 7. In the example of FIG. 1, the handle 8 is located on the distal side with respect to the grip 7, and the handle 8 is moved substantially parallel to the longitudinal axis C in the open and close motions of the handle 8, but it is not limited to this. In one embodiment, the handle 8 may be located on the proximal side with respect to the grip 7. In another embodiment, the handle 8 may be moved in a direction intersecting with (substantially perpendicular to) the longitudinal axis C in the open and close motions of the handle 8. Furthermore, in one embodiment, an operation member such as a rotation knob is attached to the housing 3 and the rotation knob is rotated about the longitudinal axis C, such that the shaft 2 and the grasping unit 5 may rotate together around the longitudinal axis C with respect to the housing 3.

FIGS. 2 to 5 are views showing an example of the configuration of the grasping unit 5. The grasping unit 5 includes a pair of jaws (grasping pieces) 11 and 12. In the example of FIGS. 2 to 5, the jaw 11 is a fixed jaw that is integral with the shaft 2 or fixed to the shaft 2. Furthermore, the jaw 12 is a movable jaw that is attached to the distal portion (jaw 11) of the shaft 2 so as to be rotatable about a rotation axis R. Furthermore, inside the shaft 2, a movable member 13 extends along the longitudinal axis C. The proximal portion of the movable member 13 is connected to the handle 8 inside the housing 3. Furthermore, the distal portion of the movable member 13 is connected to the jaw 12 (movable jaw). The movable member 13 is moved along the longitudinal axis C by opening or closing the handle 8 with respect to the grip 7. Therefore, the jaw 12 pivots about the rotation axis R, and the jaws 11 and 12 are opened or closed. Since the jaws 11 and 12 are operable and closable, the treatment target can be grasped between the jaws 11 and 12.

Figure 2:
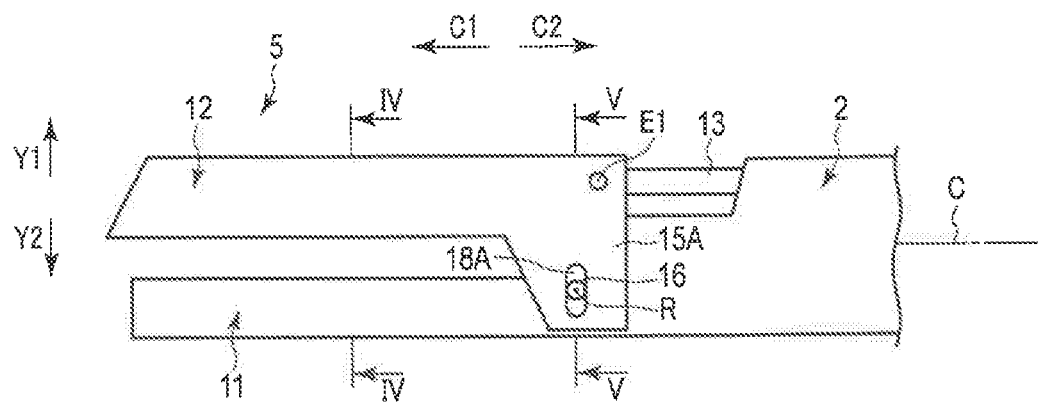
FIG. 2 is a schematic view of a grasping unit according to the first embodiment, viewed from one side in a width direction.
Figure 3:
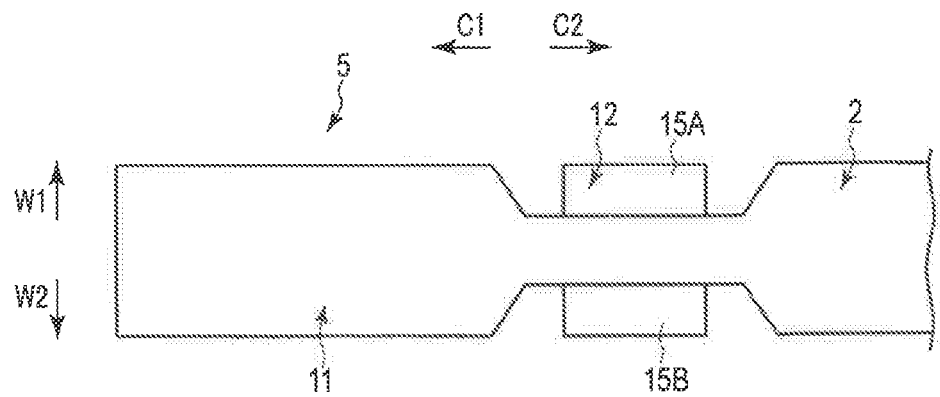
FIG. 3 is a schematic view of the grasping unit according to the first embodiment, viewed from one side in an open and close direction.
Figure 4:
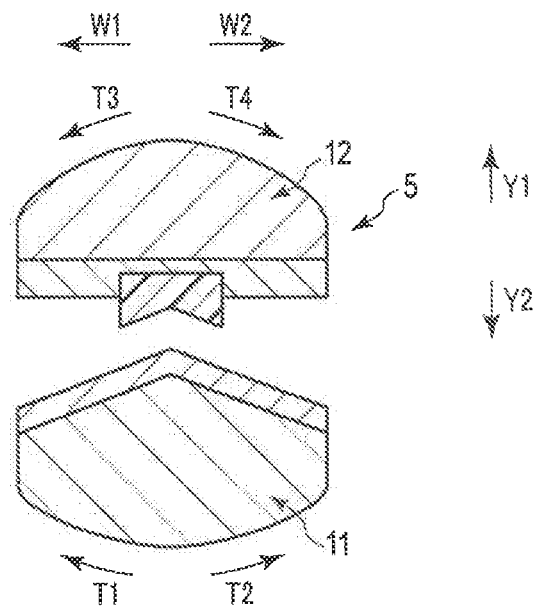
FIG. 4 is a cross-sectional view taken along IV-IV in FIG. 2.
Figure 5:
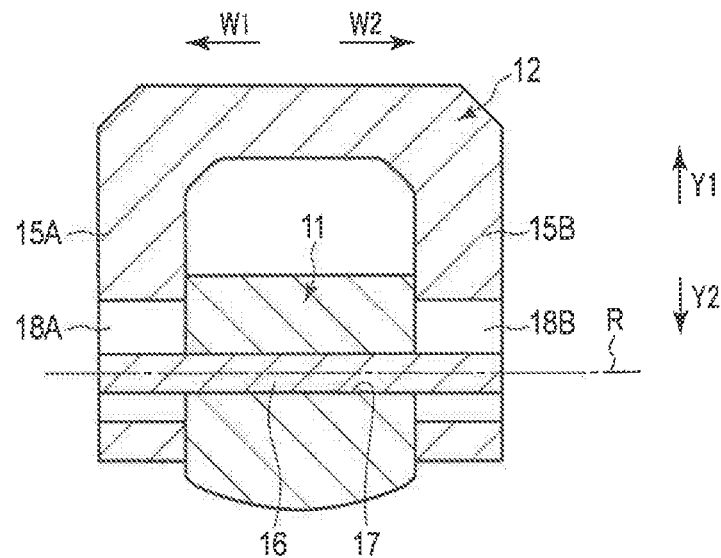
FIG. 5 is a cross-sectional view taken along V-V in FIG. 2.

The direction along the longitudinal axis C is set as the longitudinal direction of the grasping unit 5 (directions indicated by an arrow C1 and an arrow C2), and the moving direction of the jaws 12 when the jaws 11 and 12 are opened or closed is set as the open and close direction of the grasping unit 5 (directions indicated by an arrow Y1 and an arrow Y2). The open and close direction of the grasping unit 5 intersects with (is substantially perpendicular to) the longitudinal direction of the grasping unit 5. Furthermore, the direction intersecting with (substantially perpendicular to) the longitudinal direction of the grasping unit 5 and intersecting with (substantially perpendicular to) the open and close direction of the grasping unit 5 is set as the width direction of the grasping unit 5 (directions indicated by arrows W1 and W2). A roll direction of the jaw 11 (directions indicated by arrows T1 and T2) that is the direction around the central axis of the jaw 11 is defined, and a roll direction of the jaw 12 (directions indicated by an arrow T3 and an arrow T4) that is the direction around the central axis of the jaw 12 is defined. FIG. 2 shows a state where the grasping unit 5 is viewed from one side in the width direction, and FIG. 3 shows a state where the grasping unit 5 is viewed from the side (arrow Y2 side) where the jaw 12 (movable jaw) is closed, in the open and close direction of the grasping unit 5. Furthermore, FIG. 4 shows a cross section taken along IV-IV in FIG. 2, and FIG. 5 shows a cross section, taken along V-V in FIG. 2. In the present embodiment, the rotation axis R that is the rotation center of the open and close motion of the jaw 12 extends substantially in parallel to the width direction of the grasping unit 5.

In the example of FIGS. 2 to 5, a connection position E1 of the movable member 13 to the jaw 12 with respect to the rotation axis R is located on the side where the jaw 12 is opened (arrow Y1 side). Furthermore, at the position where the rotation axis R passes (extends), the jaw (fixed jaw) 11 is sandwiched by projection pieces 15A and 15B of the jaw (movable jaw) 12 from both sides in the width direction. That is, at the position where the rotation axis R passes, the jaw 12 is disposed outside the jaw 11 in the width direction. However, in one embodiment, the connection position E1 of the movable member 13 to the jaw 12 with respect to the rotation axis R may be located on the side where the jaw 12 is closed (arrow Y2 side). Furthermore, in another embodiment, the jaw (movable jaw) 12 may be sandwiched by the jaw (fixed jaw) 11 from both sides in the width direction at the position where the rotation axis R passes. In this case, at the position where the rotation axis R passes, the jaw 11 is disposed outside the jaw 12 in the width direction. Furthermore, in another embodiment, the connection position E1 of the movable member to the jaw 12 with respect to the rotation axis R is located on the side where the jaw 12 is closed, and, at the position where the rotation axis R passes, the jaw 11 may be disposed outside the jaw 12 in the width direction.

Furthermore, in the present embodiment, the jaw 12 is attached to the distal portion (jaw 11) of the shaft 2 through the pin member 16. The central axis of the pin member 16 is the rotation axis R of the jaw 12, and the pin member 16 defines the rotation axis R of the jaw 12. In the present embodiment, the pin member 16 is a single straight pin, and the cross-sectional area substantially perpendicular to the central axis becomes uniform over the entire length in the direction along the central axis. Furthermore, in the example of FIGS. 2 to 5, a hole (first hole) 17 is formed along the width direction in the jaw (first jaw) 11 located inside in the width direction at the position where the rotation axis R passes among the jaws 11 and 12. The hole 17 passes through the jaw 11 in the width direction. Furthermore, in the present embodiment, the diameter of the hole 17 is the same as or substantially the same as the outer diameter of the insertion portion of the pin member 16 into the hole 17, and the cross-sectional area of the hole 17 is the same as or substantially the same as the cross-sectional area substantially perpendicular to the central axis of the insertion portion of the pin member 16 into the hole 17.

Furthermore, in the example of FIGS. 2 to 5, holes (second holes) 18A and 18B are formed along the width direction in the jaw (second jaw) 12 located outside in the width direction at the position where the rotation axis R passes among the jaws 11 and 12. The hole 18A is formed in the projection piece 15A disposed on one side in the width direction with respect to the jaw 11 at the position where the rotation axis R passes. In addition, the hole 18B is formed in the projection piece 15B disposed on the other side in the width direction with respect to the jaw 11 at the position where the rotation axis R passes. The hole 18A passes through the projection piece 15A in the width direction, and the hole 18B passes through the projection piece 15B in the width direction. With the above-described configuration, the holes (second holes) 18A and 18B are provided outside the hole (first hole) 17 in the width direction at the position where the rotation axis P passes. The cross-sectional area of each of the holes 18A and 18B is larger than the cross-sectional area of the hole 17. In one embodiment, each of the holes 18A and 18B is formed in an elongated hole that is larger than the hole 17 in the dimension along the open and close direction of the grasping unit 5. In another embodiment, each of the holes 18A and 18B is formed in an elongated hole that is larger than the hole 17 in the dimension along the longitudinal direction of the grasping unit 5. In yet another embodiment, each of the holes 18A and 18B is formed in a clearance hole that is larger than the hole 17 in both the dimension along the open and close direction and the dimension along the longitudinal direction. In addition, the cross-sectional area of each of the holes 18A and 18B is larger than the cross-sectional area substantially perpendicular to the central axis of the insertion portion of the pin member 16 into the holes 18A and 18B.

Furthermore, in the embodiment in which the jaw (fixed jaw) 11 is located outside the jaw (movable jaw) 12 in the width direction at the position where the rotation axis R passes, the hole (first hole) corresponding to the hole 17 is formed in the jaw (first jaw) 12. The holes (second holes) corresponding to the holes 18A and 18B are formed in the jaw (second jaw) 11, and the cross-sectional area of the holes (second holes) formed in the jaw 11 is larger than the cross-sectional area of the hole (first hole) formed in the jaw 12. Therefore, in any of the embodiments, the first hole (17) is formed on one of the jaws 11 and 12 located inside in the width direction at the position where the rotation axis R passes. The second holes (18A, 18B) having a larger cross-sectional area than that of the first hole (17) is formed on the other of the jaws 11 and 12 located outside in the width direction at the position where the rotation axis R passes.

The cross-sectional area of the hole 17 is the same as or substantially the same as the cross-sectional area substantially perpendicular to the central axis of the insertion portion of the pin member 16 into the hole 17. Therefore, by inserting the pin member 16 into the hole 17, the pin member 16 is fixed to the jaw (jaw 11 in the present embodiment) in which the hole 17 is formed. In addition, the pin member 16 is joined to the jaw (jaw 12 in the present embodiment), in which the holes 18A and 18B are formed, at or near the respective edges of the holes 18A and 18B. The pin member 16 is joined to the jaw 12 by laser welding, brazing, or caulking.

In addition, in a system in which the treatment instrument 1 is used, an operation button attached to the housing 3 or a foot switch or the like separate from the treatment instrument is provided as an operation member (not shown). Electrical energy is supplied to the treatment instrument 1 from an energy source device (not shown) separate from the treatment instrument 1 based on the operation of the operation member, and treatment energy is applied to the treatment target that is grasped between the jaws 11 and 12 in the same manner as in a well-known treatment instrument. In one embodiment, electric energy is supplied to the jaws 11 and 12, and a high frequency current flows as treatment energy through the treatment target between the jaws 11 and 12. Furthermore, in another embodiment, electric energy is supplied to a heating element (not shown) provided in the grasping unit 5 to generate heat in the heating element. The heat generated in the heating element is given to the treatment target to be grasped as treatment energy. Furthermore, in another embodiment, both the high frequency current and the heat may be able to be supplied to the treatment target as treatment energy.

Next, a manufacturing method of the grasping unit 5 will be described. In the present embodiment, when manufacturing the grasping unit 5, the hole (first hole) 17 is formed in the jaw 11, and the holes (second holes) 18A and 18B having a larger cross-sectional area than that of the hole 17 are formed in the jaw 12. The pin member 16 is inserted into the hole 17 and the holes 18A and 18B. At this time, the in member 16 is inserted into the holes 17, 18A, and 16B in a state where the holes 18A and 18B are located outside the hole 17 in the width direction of the grasping unit 5. The pin member 16 extends substantially parallel to the width direction of the grasping unit 5. Therefore, at the position where the pin member 16 extends, the jaw (second jaw) 12 in which the holes 18A and 18B are formed are located outside with respect to the jaw (first jaw) 11 in which the hole 17 is formed in the width direction. In addition, the cross-sectional area of the hole 17 is formed to be the same as or substantially the same as the cross-sectional area substantially perpendicular to the central axis of the insertion portion of the pin member 16 into the hole 17. Therefore, by inserting the pin member 16 into the hole 17, the pin member 16 is fixed with respect to the jaw 11 in which the hole 17 is formed, that is, the jaw (first jaw) 11 located inside in the width direction at the position where the pin member 16 extends. In addition, the cross-sectional area of the holes 18A and 18B is larger than the cross-sectional area of the hole 17. Therefore, even if the pin member 16 is inserted into the holes 18A and 18B, the jaw 12 in which the holes 18A and 18B are formed, that is, the jaw (second jaw) 12 located outside with respect to the width direction at the position where the pin member 16 extends is movable relative to the pin member 16 and the jaw 11.

In a state where the pin member 16 is inserted into the holes 17, 18A, and 18B, the relative positions of the jaws 11 and 12 are adjusted to predetermined positions. In a state where the pin member 16 is inserted into the holes 17, 18A, and 18B, the jaw (second jaw) 12 in which the holes 18A and 18B are formed are movable relative to the jaw (first jaw) 11 in which the hole 17 is formed and the pin member 16. Therefore, the relative positions of the jaws 11 and 12 are adjusted by changing the positions of the hole 17 and the pin member 16 with respect to the holes 18A and 18B in a state where the position of the hole 17 with respect to the pin member 16 is fixed. Furthermore, in the present embodiment, the jaw 11 is a fixed jaw, and the jaw 12 is a movable jaw. Therefore, when adjusting the relative positions of the jaws 11 and 12, the position of the jaw 12 with respect to the shaft 2 is changed by changing the positions of the hole 17 and the pin member 16 with respect to the holes 18A and 18B.

In the embodiment in which the hole 17 is formed in the jaw (movable jaw) 12 and the holes 18A and 18B larger than the hole 17 are formed in the jaw (fixed jaw) 11, that is, in the embodiment in which the jaw 11 is located outside the jaw 12 in the width direction at the position where the pin member 16 extends, the relative positions of the jaws 11 and 12 are adjusted by changing the positions of the hole 17 and the pin member 16 with respect to the holes 18A and 18B in a state where the position of the hole 17 with respect to the pin member 16 is fixed. Therefore, when adjusting the relative positions of the jaws 11 and 12, the positions of the jaw 12 and the pin member 16 with respect to the shaft 2 are changed by changing the positions of the hole 17 and the pin member 16 with respect to the holes 18A and 18B.

Figure 6:
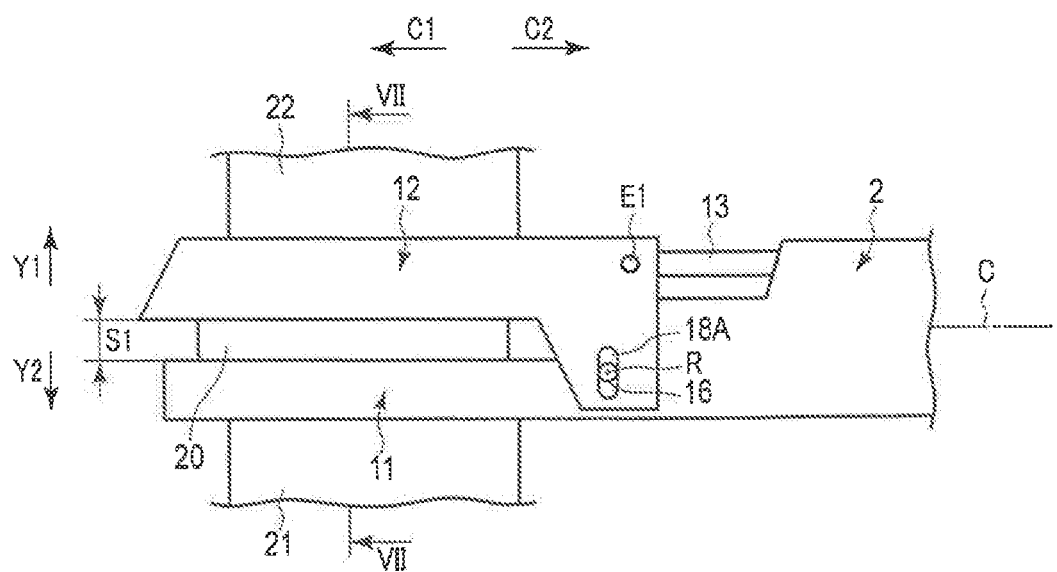
FIG. 6 is a schematic view showing an example of a state where a clearance between a pair of jaws according to the first embodiment is adjusted.
Figure 7:
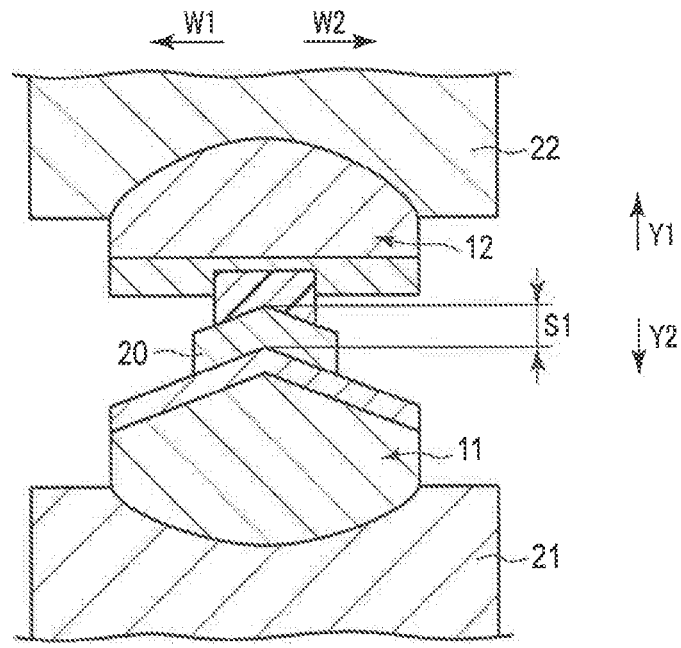
FIG. 7 is a cross-sectional view taken along VII-VII in FIG. 6.

FIGS. 6 and 7 show a state where a clearance S1 between the jaws 11 and 12 is adjusted as an example of adjustment of the relative positions of the jaws 11 and 12. FIG. 6 shows a state when viewed from one side in, the width direction of the grasping unit 5, and FIG. 7 shows a VII-VII cross section in FIG. 6. In addition, when the adjustment of the clearance S1 is performed, the holes 18A and 18B are formed in the elongated holes or the clearance holes that are larger than the hole 17 (the insertion portions of the pin member 16 into the holes 18A and 18B in the dimension along the open and close direction of the grasping unit 5. As shown in FIGS. 6 and 7, the adjustment of the clearance S1 is performed in a state where an adjustment member 20 such as a plate member is bitten between the jaws 11 and 12. A pressing member 21 presses the jaw 11 toward the jaw 12 from the back surface side, and a pressing member 22 presses the jaw 12 toward the jaw from the back surface side. In one embodiment, the pressing members 21 and 22 are formed by clips. In another embodiment, each of the pressing members 21 and 22 is biased in a state where the corresponding one of the jaws 11 and 12 is pressed by a spring member (not shown) or the like.

The adjustment member 20 has a uniform dimension (thickness) in the open and close direction of the grasping unit 5 from one end (proximal end) to the other end (distal end) in the longitudinal direction of the grasping unit 5. Therefore, by biting the adjustment member 20 between the jaws 11 and 12, the jaws 11 and 12 become parallel or substantially parallel to each other, and the clearance S1 between the jaws 11 and 12 is adjusted to a predetermined clearance. That is, the adjustment member 20 adjusts a gap between the jaws 11 and 12 to a predetermined clearance in a state where the jaws 11 and 12 are parallel to each other. In one embodiment, the dimension (thickness) of the adjustment member 20 in the open and close direction of the grasping unit 5 is 0.1 mm, and the clearance S1 between the jaws 11 and 12 in a state where the jaws 11 and 12 are parallel to each other is adjusted to a predetermined clearance of 0 mm or more and 0.2 mm or less.

Figure 8:
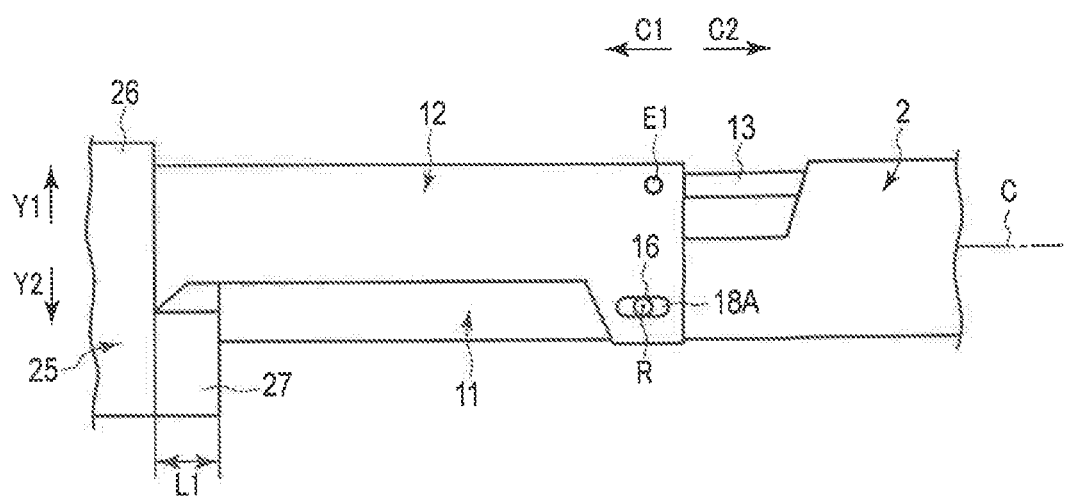
FIG. 8 is a schematic view show an example state where a positional relationship of the pair of jaws according to the first embodiment with respect to each other in a longitudinal direction of the grasping unit.

FIG. 8 shows, as an example of the adjustment of the relative positions of the jaws 11 and 12, a state where the positional relationship of the jaws 11 and 12 with respect to each other in the longitudinal direction of the grasping unit 5 is adjusted. FIG. 8 shows a state when viewed from one side in the width direction of the grasping unit 5. In addition, when the adjustment of the relative positional relationship of the jaws 11 and 12 in the longitudinal direction is performed, the holes 18A and 18B are formed in the elongated holes or the clearance holes that are larger than the hole 17 (the insertion portions of the pin member 16 into the holes 18A and 18B) in the dimension along the longitudinal direction of the grasping unit 5. As shown in FIG. 8, when adjusting the relative positional relationship of the jaws 11 and 12 in the longitudinal direction, the jaws 11 and 12 are closed, and the adjustment member 25 such as a plate member abuts on the jaws 11 and 12 from the distal side. In one embodiment, the adjustment member 25 may be biased by a spring member (not shown) in a state where the jaws 11 and 12 are pressed towards the proximal side.

In the example of FIG. 8, the adjustment member 25 includes a base 26, and a projection 27 projecting from the base 26 to the proximal side. When adjusting the relative positional relationship of the jaws 11 and 12 in the longitudinal direction, the base 26 presses the jaw (movable jaw) 12, and the projection 27 presses the jaw (fixed jaw) 11. By adjusting the relative positional relationship of the jaws 11 and 12 in the longitudinal direction, the jaw 12 projects from the distal end of the jaw 11 to the distal side by a predetermined dimension. That is, a projection dimension 11 of the jaw (movable jaw) 12 with respect to the jaw (fixed jaw) 11 is adjusted to a predetermined dimension.

Figure 9:
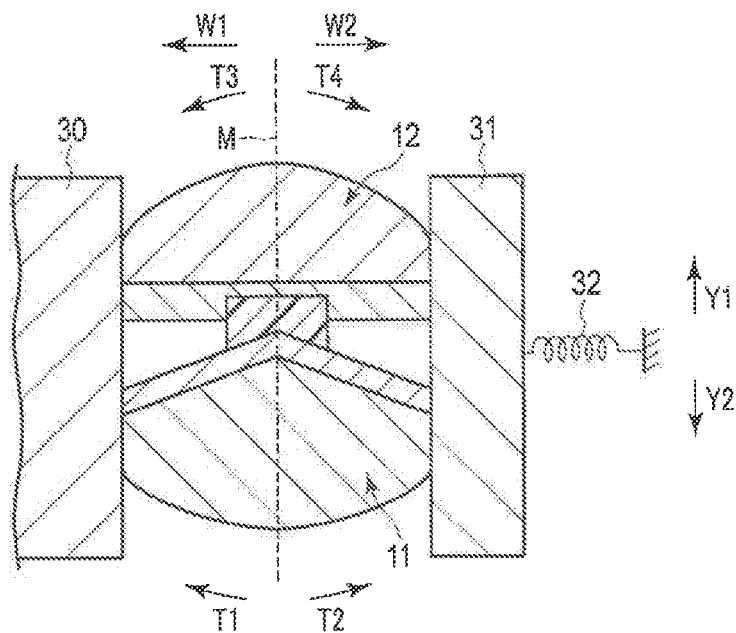
FIG. 9 is a schematic view showing an example of a state, where a positional relationship of one jaw with respect to the other jaw in a direction around a central axis of the one of the pair of jaws according to the first embodiment is adjusted.

FIG. 9 shows, as an example of the adjustment of the relative positions of the jaws 11 and 12, a state where the positional relationship of the jaw 12 with respect to the jaw 11 in the direction around the central axis of each of the jaws 11 and 12 (the roll direction of each of the jaws 11 and 12). FIG. 9 shows a cross section substantially perpendicular to the longitudinal direction of the grasping unit 5. As shown in FIG. 9, when adjusting the position of the jaw 12 with respect to the jaw 11 in the direction around the central axis of each of the jaws 11 and 12, an adjustment member 30 such as a plate member abuts on the jaws 11 and 12 from one side in the width direction of the grasping unit 5. An adjustment member 31 such as a plate member abuts on the jaws 11 and 12 from the other side in the width direction. That is, the jaws 11 and 12 are sandwiched between the adjustment members 30 and 31 in the width direction. In one embodiment, one of the adjustment members 30 and 31 (the adjustment member 31 in the example of FIG. 9) is biased by a spring member 32 to press the jaws 11 and 12.

By adjusting the position of the jaw 12 with respect to the jaw 11 in the direction around the central axis of each of the jaws 11 and 12, for example, the clearance between the jaws 11 and 12 is formed substantially symmetrically about a central plane M with respect to the width direction of the grasping unit 5. Furthermore, as described above, by adjusting the position of the jaw (second jaw) 12 with respect to the jaw (first jaw) 11 in the direction around the central axis of each of the jaws 11 and 12, the relative positions of the jaws 11 and 12 with respect to the width direction of the grasping unit 5 is also adjusted.

Figure 10:
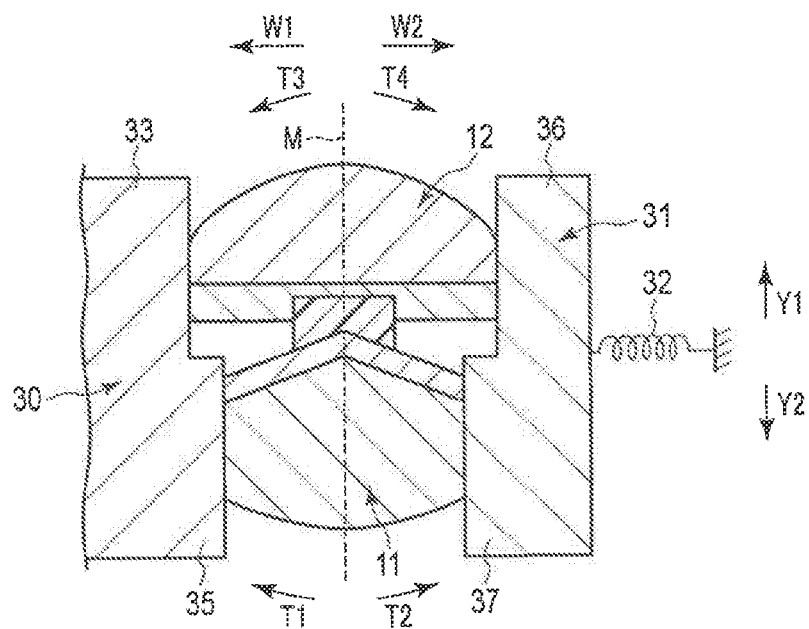
FIG. 10 is a schematic view showing an example, different from FIG. 9, of a state where a positional relationship of one jaw with respect to the other jaw in a direction around a central axis of the one of the pair of jaws according to the first embodiment is adjusted.

In the embodiment in which the dimension of the jaw 11 in the width direction and the dimension of the jaw 12 in the width direction are different from each other, as shown in FIG. 10, the adjustment member 30 is provided with a base 33 and a projection 35 projecting inward in the width direction from the base 33, and the adjustment member 31 is provided with a base 36 and a projection 37 projecting inward in the width direction from the base 36. The bases 33 and 36 abut on one (the jaw 12 in FIG. 10) of the jaws 11 and 12 that has a larger dimension in the width direction, and the projections 35 and 37 abut on the other (the jaw 11 in FIG. 10) of the jaws 11 and 12 that has a smaller dimension in the width direction. Thus, in the example of FIG. 10, the jaw 12 having a larger dimension in the width direction is sandwiched between the bases 33 and 36 in the width direction, and the jaw 11 having a smaller dimension in the width direction is sandwiched between the projections 35 and 37 in the width direction. Therefore, even if the dimensions of the jaws 11 and 12 in the width direction are different from each other, the position of the jaw (second jam) 12 with respect to the jaw (first jaw) in the direction around the central axes of the respective jaws 11 and 12 is adjusted, and the relative positions of the jaws 11 and 12 with respect to the width direction of the grasping unit 5 are also adjusted.

Figure 11:
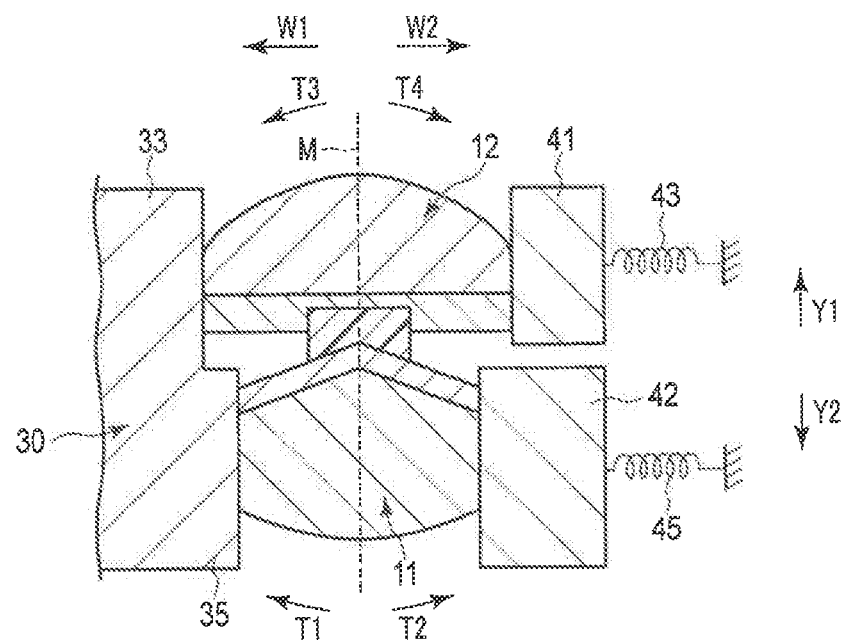
FIG. 11 is a schematic view showing an example, different from FIGS. 9 and 10, of a state where a positional relationship of one jaw with respect to the other jaw in a direction around a central axis of the one of the pair of jaws according to the first embodiment is adjusted.

Furthermore, when the dimensions of the jaws 11 and 12 in the width direction are different from each other, adjustment members 41 and 42 may be provided instead of the adjustment member 31 as shown in FIG. 11. In this case, the adjustment member 41 is biased by the spring member 43 to press the jaw 12, and the adjustment member 42 is biased by the spring member 45 to press the jaw 11. The jam 12 having a larger dimension in the width direction is sandwiched between the base 33 of the adjustment member 30 and the adjustment member 41 in the width direction, and the jaw 11 having a smaller dimension in the width direction is sandwiched between the projection 35 of the adjustment member 30 and the adjustment member 42 in the width direction.

When adjusting the relative positions of the jaws 11 and 12 to predetermined positions, at least one of the adjustment of the clearance S1 between the jaws 11 and 12 described above, the adjustment of the positions of the jaws 11 and 12 with respect to each other in the longitudinal direction of the grasping unit 5, the adjustment of the positional relationship of the jaw 12 with respect to the jaw 11 in the direction around the central axes of the respective jaws 11 and 12 (the roll direction of each of the jaws 11 and 12), and the adjustment of the positions of the jaws 11 and 12 with respect to each other in the width direction of the grasping unit 5 is performed. In a state where the jaws 11 and 12 are adjusted to the predetermined positions, the pin member 16 is joined to the jaw 12 in which the holes (second holes) 18A and 18B are formed.

Figure 12:
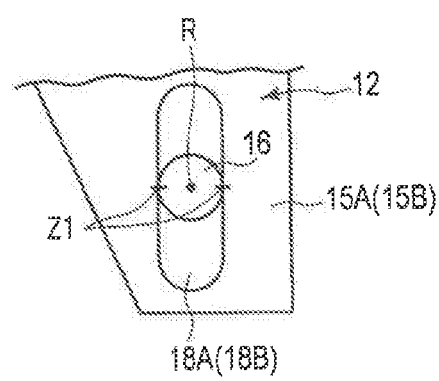
FIG. 12 is a schematic view showing a joint portion of a pin member according to the first embodiment to a jaw in which a large hole (second hole) is formed.

FIG. 12 is a view showing the joint portion of the pin member 16 to the jaw 12. As shown in FIG. 12, the pin member 16 is joined to the jaw (jaw 12 in the present embodiment), in which the holes 18A and 18B are formed, at or near the respective edges of the holes 18A and 18B. The pin member 16 is joined to the jaw 12 by laser welding, brazing, or caulking. For example, when the pin member 16 is a single straight pin and the holes 18A and 18B are elongated holes along the longitudinal direction or the open and close direction of the grasping unit 5, the outer periphery of the pin member 16 is joined to the edge of each of the holes 18A and 18B at the joint portion Z1. In a state where the jaws 11 and 12 are adjusted to the predetermined positions, the pin member 16 is joined to the jaw 12 to form the grasping unit 5 in which the jaws 11 and 12 are adjusted to the predetermined positions, that is, the relative positions of the jaws 11 and 12 are appropriately adjusted. Furthermore, the pin member 16 is joined to the jaw 12 to define the rotation axis R of the jaw 12.

Next, the function and effect of the grasping unit 5 manufactured by the manufacturing method of the present embodiment will be described. When the treatment target is treated by using the treatment instrument 1 including the grasping unit 5, the operator grasps the housing 3 and inserts the grasping unit (end effector) 5 into a body cavity such as an abdominal cavity. The treatment target is disposed between the pair of jaws (grasping pieces) 11 and 12, and the handle 8 is closed relative to the grip 7. Therefore, the jaws 11 and 12 are closed, and the treatment target is grasped between the jaws 11 and 12. In this state, the operator performs the operation with the operation member such as the foot switch, such that the electric energy is supplied from the energy source device (not shown) to the treatment instrument 1, and as described above, the treatment energy such as the high frequency current and the heat is applied to the treatment target grasped between the jaws 11 and 12.

For example, as the treatment using the treatment instrument 1, the grasped treatment target is incised simultaneously with coagulation by bringing each of the jaws 11 and 12 into contact with the treatment target over the most portion from the distal portion to the proximal portion in the longitudinal direction, grasping the treatment target between the jaws 11 and 12, and applying the treatment energy thereto. In the present embodiment, in the manufacture of the grasping unit 5, the relative positions of the jaws 11 and 12 can be adjusted as described above, and the clearance S1 between the jaws 11 and 12 that are parallel to each other can be adjusted to the predetermined clearance. By setting the predetermined clearance to an appropriate magnitude (for example, 0 mm to 0.2 mm) in the treatment, the grasping force acting on the treatment target, is uniform in the longitudinal direction from the distal portion to the proximal portion in the treatment in which each of the jaws 11 and 12 is brought into contact with the treatment target over the most portion from the distal portion to the proximal portion in the longitudinal direction of the grasping unit 5. Since the treatment is performed in a state where the grasping force is uniform from the distal portion to the proximal portion in the longitudinal direction, the incision and coagulation properties of the treatment target are improved, and the treatment performance is improved.

Furthermore, as the treatment using the treatment instrument 1, only the distal portion in each of the jaws 11 and 12 is brought into contact with the treatment target to grasp the treatment target. In the present embodiment, in the manufacture of the grasping unit 5, it is possible to adjust the relative positions of the jaws 11 and 12 as described above, and it is possible to adjust the relative positions of the jaws 11 and 12 in the longitudinal direction of the grasping unit 5. By adjusting the relative positions of the jaws 11 and 12 in the longitudinal direction of the grasping unit 5, the projection dimension L1 of the jaw (movable jaw) 12 to the distal side with respect to the jaw (fixed jaw) 11 is adjusted to a predetermined dimension. By setting the projection dimension L1 to an appropriate magnitude in the treatment, the treatment target is stably grasped between the jaws 11 and 12 in the treatment in which only the distal portion is brought into contact with the treatment target in each of the jaws 11 and 12. This improves the treatment performance in the treatment in which only the distal portion in each of the jaws 11 and 12 is brought into contact with the treatment target.

Furthermore, as the treatment using the treatment instrument 1, the high frequency current may be flowed through the treatment target grasped between the jaws 11 and 12. In the present embodiment, in the manufacture of the grasping unit 5, it is possible to adjust the relative positions of the jaws 11 and 12 as described above, and it is possible to adjust the position of the jaw 12 with respect to the jaw 11 in the direction around the central axis of each of the jaws 11 and 12 (the roll direction of each of the jaws 11 and 12) and the relative positions of the jaws 11 and 12 in the width direction of the grasping unit 5. By adjusting the position of the jaw 12 with respect to the jaw 11 in the direction around the central axis of each of the jaws 11 and 12 and the relative positions of the jaws 11 and 12 in the width direction of the grasping unit 5, the clearance between the jaws 11 and 12 is formed substantially symmetrically about the central plane M with respect to the width direction of the grasping unit 5. Therefore, for example, the high frequency current flows uniformly to the treatment target in the range grasped between the jaws 11 and 12 in the width direction of the grasping unit 5, and the treatment energy is uniformly applied to the treatment target in the range grasped between the jaws 11 and 12 in the width direction of the grasping unit 5. For example, it is possible to effectively prevent the current density of the high frequency current from being excessively high on one side with respect to the central plane M in the width direction and prevent the current density of the high frequency current from being excessively low on the other side with respect to the central plane N in the width direction. The treatment performance in the treatment using the treatment energy is improved by uniformly applying the treatment energy to the treatment target in the range grasped between the jaws 11 and 12 in the width direction of the grasping unit 5.

As described above, in the present embodiment, at the time of the manufacture, the treatment performance in the treatment using the grasping unit 5 is appropriately secured by appropriately adjusting the relative positions of the jaws 11 and 12 to the predetermined positions.

Modifications

Figure 13:
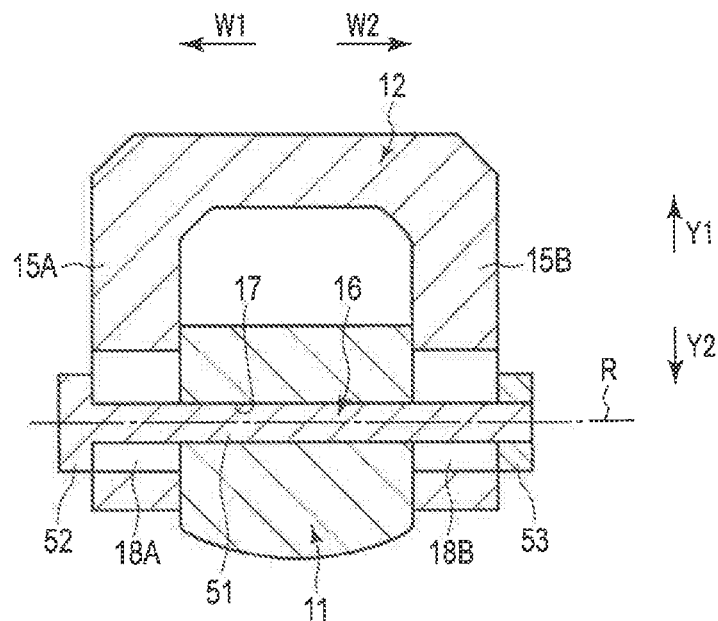
FIG. 13 is a schematic view showing a grasping unit according to a first modification in a cross section substantially perpendicular to a longitudinal direction and passing through a pin member.
Figure 14:
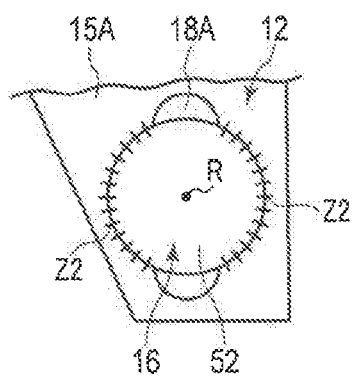
FIG. 14 is a schematic view showing a joint portion of the pin member according to the first modification to a jaw in which a large hole (second hole) is formed.
Figure 15:
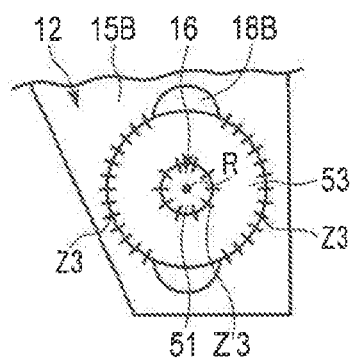
FIG. 15 is a schematic view showing a joint portion of a washer attached, to the pin member according to the first modification to the jaw in which the large hole (second hole) is formed.

In the first embodiment, the pin member 16 is a single straight pin, but is not limited to this. For example, in the first modification shown in FIGS. 13 to 15, a pin member 16 includes a pin main body 51 inserted into holes 17, 18A, and 18B, and a flange 52 that is larger than the pin main body 51 in the cross-sectional area substantially perpendicular to the central axis of the pin member 16. The flange 52 is not inserted into the hole (second hole) 18A and is disposed outside the hole 18A in a width direction of a grasping unit 5. The flange 52 abuts on a projection piece 15A of a jaw 12 from the outside in the width direction. The flange 52 is joined to the jaw 12, which is located outside in the width direction at a position where a rotation axis R passes, in the abutting portion to the projection piece 15A, that is, in the vicinity of the hole 18A. That is, a joint portion Z2 between the flange 52 of the pin member 16 and the jaw 12 is formed in the vicinity of the hole 18A.

Furthermore, in the present modification, a washer 53 is joined at a portion that projects outward from the hole 18B in the width direction on the outer peripheral surface of the pin main body 51. The area of the range surrounded by the outer periphery of the washer 53 is larger than the cross-sectional area of the pin main body S1 substantially perpendicular to the central axis of the pin member 16. The washer 53 is not inserted into the hole (second hole) 18B and is disposed outside the hole 18B in the width direction of the grasping unit 5. The washer 53 abuts on the projection piece 15B of the jaw 12 from the outside in the width direction. The washer 53 is joined to the jaw 12, which is located outside in the width direction, at the position where the rotation axis R passes, in the abutting portion to the projection piece 15B, that is, in the vicinity of the hole 18B. That is, a joint portion Z3 between the washer 53 and the jaw 12 is formed in the vicinity of the hole 18B. After the washer 53 and the jaw 12 are joined at the joint portion Z3, the pin main body 51 and the washer 53 may be joined. That is, a joint portion Z'3 between the pin main body 51 and the washer 53 may be formed. Therefore, a rattling between the pin main body 51 and the washer 53 can be further suppressed.

Figure 16:
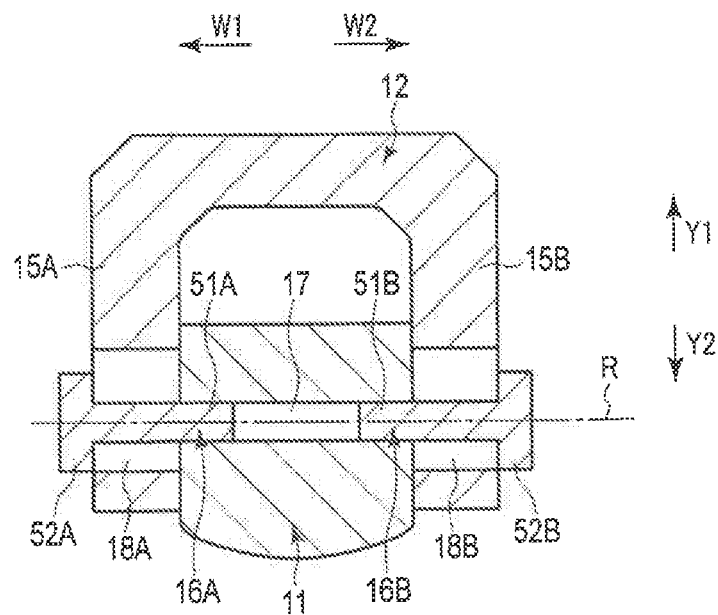
FIG. 16 is a schematic view showing a grasping unit according to a second modification in a cross section substantially perpendicular to a longitudinal direction and passing through a pin member.

Furthermore, in a second modification shown in FIG. 16, two pin members 16A and 16B are provided. The pin member 16A is provided with a pin main body 51A and a flange 52A, and the pin member 16B is provided with a pin main body 51B and a flange 52B. In the pin member 16A, the pin main body 51A is inserted into holes 17 and 18A, and the flange 52A is disposed outside the hole 18A in the width direction. The flange 52A is joined to a jaw 12 in the vicinity of the hole 18A. Furthermore, in the pin member 16B, the pin main body 51B is inserted into the holes 17 and 18B, and the flange 52B is disposed outside the hole 18B in the width direction. The flange 52B is joined to the jaw 12 in the vicinity of the hole 18B.

Figure 17:
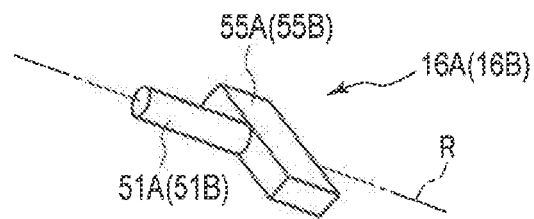
FIG. 17 is a schematic view showing a pin member according to a third modification.
Figure 18:
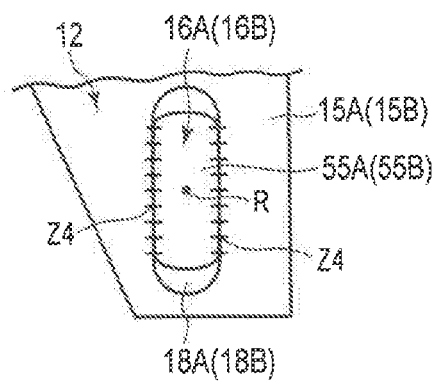
FIG. 18 is a schematic view showing a joint portion of the pin member according to the third modification to a jaw in which, a large hole (second hole) is formed.

In a third modification shown in FIGS. 17 and 18, each of pin members 16A and 16B includes a rectangular cross-sectional portion (55A; 55B) having a substantially rectangular shape in the cross section substantially perpendicular to the central axis of the pin member (16A; 16B), instead of the flanges (52A; 52B). The cross-sectional area of each of the rectangular cross-sectional portions 55A and 55B approximately perpendicular to the central axis of the pin member (16A; 16B) is larger than the cross-sectional area of each of the pin main bodies 51A and 51B substantially perpendicular to the central axis of the pin member (16A; 16B). In the present modification, each of the rectangular cross-sectional portions 55A and 55B abuts on the edge of the corresponding one of the holes 18A and 18B. Each of the rectangular cross-sectional portions 55A and 55B is connected to the jaw 12, which is located outside in the width direction at the position where the rotation axis R passes, at the abutting portion to the edge of the corresponding one of the holes 18A and 18B. That is, at each edge of the holes 18A and 18B, a joint Z4 between the corresponding one of the rectangular cross-sectional portions 55A and 55B and the jaw 12 is formed.

In the first to third modifications described above, the joining range between the pin member (16; 15A, 16B) and the jaw 12 is larger than that in the first embodiment. Therefore, the jaws 11 and 12 are firmly connected through the pin member (16; 16A, 16B). Therefore, even if the amount of the grasping force between the jaws 11 and 12 increases, the joining between the jam 12 and the pin member (16; 16A, 16B) is less likely to come off, and the connection between the jaws 11 and 12 is less likely to come off. Furthermore, from the first to third modifications described above, various known configurations can be applied to the number of pin members (16; 16A, 16B), the configuration of the pin members (16; 16A, 16B), and the joint configuration between the jaw (11 or 12), which is located outside in the width direction at the position where the rotation axis R passes, and the pin member (16; 16A, 16B).

Figure 19:
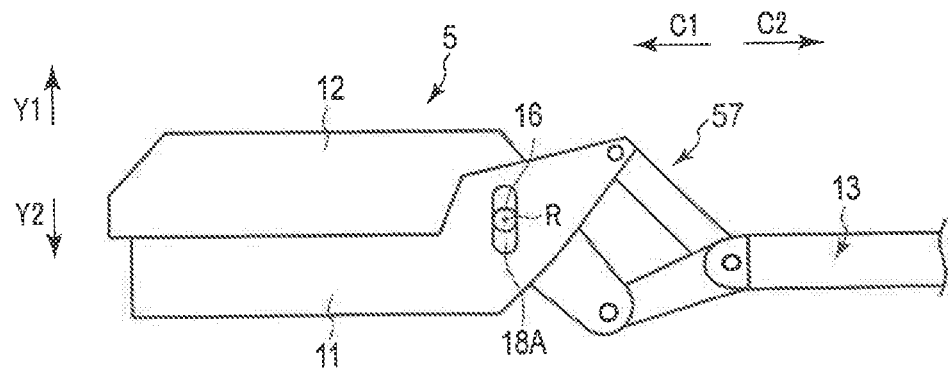
FIG. 19 is a schematic view of a grasping unit according to a fourth modification, viewed from one side in a width direction.

Furthermore, in the embodiments described above, the grasping unit 5 is a single-open type grasping unit, in which only one of the jaws 11 and 12 can rotate with respect to the shaft 2, but it is not limited to this. In a fourth modification shown in FIG. 19, the grasping unit 5 is a double-open type grasping unit in which both the jaws 11 and 12 are pivotable about the rotation axis R. That is, both the jaws 11 and 12 are movable jaws. In the present modification, the distal portion of the movable member 13 described above is connected to the jaws 11 and 12 through a link mechanism 57. In the present modification, the link mechanism 57 is actuated by opening or closing a handle 8 with respect to a grip 7 and moving the movable member 13 along a longitudinal axis C, and both the jaws 11 and 12 pivot about the rotation axis R. Due to this, the jaws 11 and 12 are opened or closed. In the present modification as well, as in the first embodiment, a hole (first hole) 17 is formed in the jaw (one of 11 and 12) located inside in the width direction at the position where the rotation axis R passes in the jaws 11 and 12. Holes (second holes) 18A and 18B having a larger cross-sectional area than that of the hole 17 are formed in the jaw (the other of 11 and 12) located outside in the width direction at the position where the rotation axis R passes in the jaws 11 and 12. The grasping unit 5 may be formed in a double-open type grasping unit by providing a cam mechanism instead of the link mechanism 57.

In the present modification as well, as described above in the first embodiment, the relative positions of the jaws 11 and 12 are adjusted, and the grasping unit 5 is manufactured. However, in the present modification, since both the jaws 11 and 12 are movable relative to the shaft 2, the position of one of the jaws 11 and 12 with respect to the shaft 2 are fixed by using a clip or the like before the relative posit ions of the jaws 11 and 12 are adjusted. When adjusting the relative positions of the jaws 11 and 12, the position of the other of the jaws 11 and 12 not fixed with respect to the shaft 2 is changed with respect to the shaft 2. Therefore, even in the double-open type grasping unit 5, the relative positions of the jaws 11 and can be appropriately adjusted at the time of the manufacture.

Figure 20:
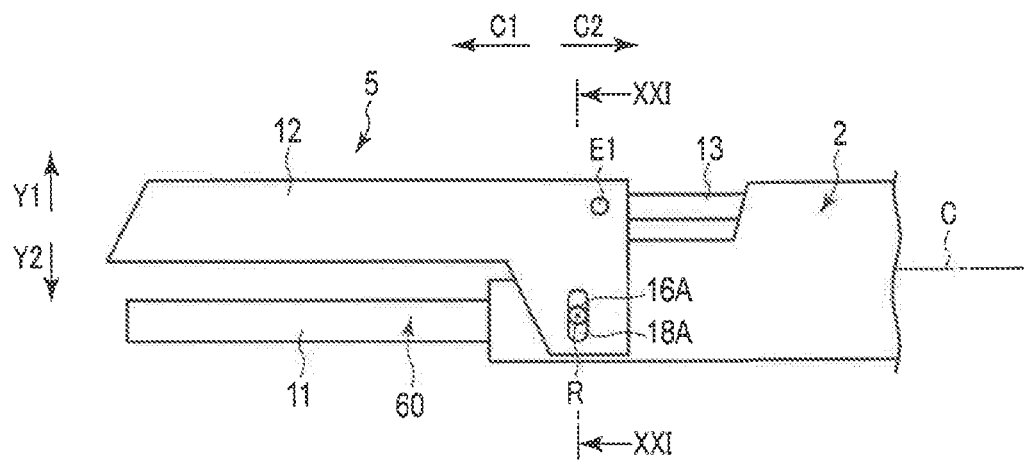
FIG. 20 is a schematic view of a grasping unit according to a fifth modification, viewed from one side in a width direction.
Figure 21:
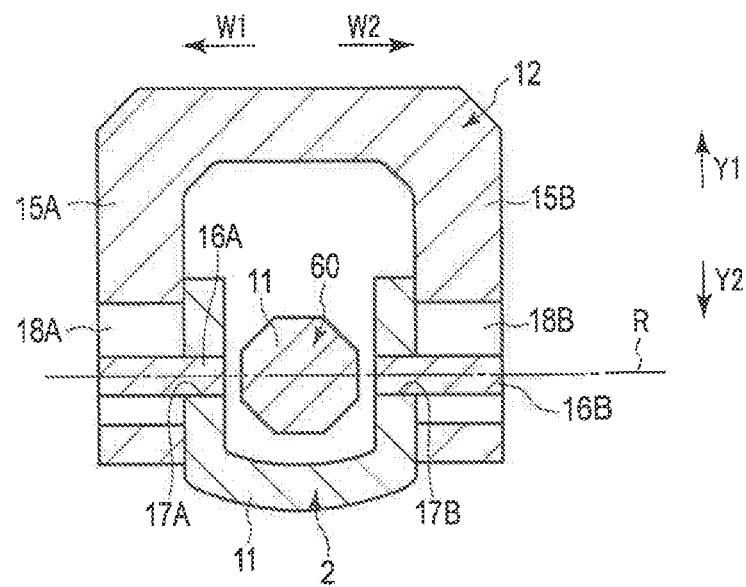
FIG. 21 is a cross-sectional view taken along XXI-XXI in FIG. 20.

Furthermore, in a fifth modification shown in FIGS. 20 and 21, a rod member 60 extends along a longitudinal axis C inside a shaft 2, and a distal portion of the rod member 60 projects from a distal end of the shaft 2 to a distal side. In the present modification, a jaw 11 is formed by the distal portion of the shaft 2 and the projecting portion of the rod member 60 from the shaft 2. Furthermore, a jaw 12 is attached to the distal portion of the shaft 2 so as to be movable about a rotation axis R. The rod member 60 is supported to the shaft 2 via a support member (not shown) disposed inside the shaft 2, and is fixed to the shaft 2. Therefore, in the present modification, the jaw 11 is fixed to the shaft 2. Furthermore, the distal portion of the movable member 13 is connected to the jaw 12 that is a movable jaw.

In the example of FIGS. 20 and 21, the jaw 12 is located outside the shaft 2 (jaw 11) in the width direction at the position where the rotation axis R passes. Therefore, holes (first holes) 17A and 17B corresponding to the hole 17 of the first embodiment are formed in the distal portion of the shaft 2 that is a part of the jaw 11. In the jaw 12, holes (second holes) 18A and 18B having a larger cross-sectional area than those of the holes 17A and 17B are formed. Therefore, in the present modification as well, the holes 18A and 18B are located outside with respect to the holes 17A and 17B in the width direction at the position where the rotation axis R passes. That is, the holes 17A and 17B are formed in the inner jaw 11 in the width direction at the position where the rotation axis R passes, and the holes 18A and 18B having a larger cross-sectional area than those of the holes 17A and 17B are formed in the outer jaw 12 in the width direction at the position where the rotation axis R passes. Furthermore, in the present modification, the pin member 16A is inserted into the holes 17A and 18A, and the pin member 16B is inserted into the holes 17B and 18B.

In one embodiment, the jaw 12 may be located inside the shaft 2 (jaw 11) in the width direction at the position, where the rotation axis R passes. In this case, the jaw 12 is located between the rod member 60 and the shaft 2 in the width direction. The holes 17A and 17B are formed in the jaw 12, and the holes 16A and 18B having a larger cross-sectional area than those of the holes 17A and 17B are formed in the distal portion of the shaft 2 that is a part of the jaw 11.

Furthermore, in the present modification, ultrasonic vibration as treatment energy can be applied to the treatment target to be grasped. In this case, an ultrasonic transducer (not shown) is provided inside the housing 3, and the proximal end of the rod member 60 is connected to the ultrasonic transducer. Furthermore, the rod member 60 is made of a material having high vibration transferability, such as a titanium alloy. The supply of the electric energy from the above-described energy source device to the ultrasonic transducer causes the ultrasonic transducer to generate the ultrasonic vibration. Therefore, the ultrasonic vibration is transmitted to the projecting portion of the rod member 60 from the shaft 2 in the jaw 11 through the rod member 60.

In the present modification as well, as described above in the first embodiment, the relative positions of the jaws 11 and 12 are adjusted, and the grasping unit 5 is manufactured. Therefore, even in the grasping unit 5 in which the rod member 60 projects from the shaft 2 in the distal side, the relative positions of the jaws 11 and 12 can be appropriately adjusted at the time of the manufacture.

In the above-described embodiments and the like, in the manufacture of the grasping unit (5), the first hole (17; 17A, 17B) is formed in the first jaw (11; 12), and the second hole (18A, 18B) larger than the first hole (17; 17A, 17B) is formed in the second jaw (12; 11). The pin member (16; 16A, 16B) defining the rotation axis (R) of the first jaw (11; 12) and/or the second jaw (12; 11) in the open and close motion between the pair of jaws (11; 12) is inserted into the first hole (17; 17A, 17B) and the second hole (18A, 18B). In a state where the pin member (16; 16A, 16B) is inserted into the first hole (17; 17A, 17B) and the second hole (18A, 18B), the relative positions of the pair of jaws (11, 12) are adjusted to predetermined positions. In a state where the first jaw (13, 12) and the second jaw (12; 11) are adjusted to the predetermined positions, the pin member (16; 16A, 16B) is joined to the second jaw (12; 11).

Additional advantages and modifications will readily occur to those skilled in the art. Therefore, the exemplary embodiments in broader aspects are not limited to the specific details and representative embodiments shown and described herein. Accordingly, various modifications may be made without departing from the spirit or scope of the general inventive concept as defined by the claims and their equivalents.

What is claimed is:

1. A manufacturing method of a grasping device of a treatment instrument that is openable and closable, the grasping device including a first jaw having a first hole and a second jaw having a second hole larger than the first hole, the method comprising:
    arranging the first jaw in between protruding portions of the second jaw, such that the second hole is located outside the first hole in a width direction of the grasping device, a cross-sectional area of the second hole is larger than a cross-sectional area of the first hole;
    inserting a pin member through both the first hole and the second hole in a state where the second hole is located outside the first hole in the width direction, the inserted pin member defining a rotation axis of the first jaw or the second jaw in an open and close motion between the first jaw and the second jaw;

adjusting positions of the first jaw and the pin member relative to the second jaw to predetermined positions while the pin member is inserted into the first hole and the second hole; and fixing the pin member to the second jaw upon positioning the first jaw and the second jaw at the predetermined positions.

2. The manufacturing method, according to claim 1, wherein the adjusting of the first jaw and the second jaw to the predetermined positions includes adjusting a gap between the first jaw and the second jaw to a predetermined clearance and adjusting the second jaw to be parallel to the first jaw.

3. The manufacturing method according to claim 2, wherein the adjusting of the gap between the first jaw and the second jaw to the predetermined clearance includes inserting and sandwiching an adjustment member between the first jaw and the second jaw.

4. The manufacturing method according to claim 1, wherein, the adjusting of the first jaw and the second jaw to the predetermined positions includes adjusting the position of the second jaw with respect to the first jaw in a longitudinal direction of the grasping device.

5. The manufacturing method according to claim 1, wherein the adjusting of the first jaw and the second jaw to the predetermined positions includes adjusting the position of the second jaw with respect to the first jaw in at least one of a direction around a central axis of each of the first jaw and the second jaw and a width direction of the grasping device.

6. The manufacturing method according to claim 1, wherein:

one of the first jaw and the second jaw is a fixed jaw integrated with or fixed to a shaft extending along a longitudinal axis, and another of the first jam and the second jaw is a movable jaw that is rotatable relative to the shaft about the rotation axis, and the adjusting of the first jaw and the second jaw to the predetermined positions includes changing the position of the movable jaw with respect to the shaft.

7. The manufacturing method according to claim 1, wherein both the first jaw and the second jaw are movable jaws that are rotatable about the rotation axis with respect to a shaft extending along a longitudinal axis, and the adjusting of the first jaw and the second jaw to the predetermined positions includes changing the position of one of the movable jaws with respect to the shaft in a state where the position of another of the movable jaws with respect to the shaft is fixed.

8. The manufacturing method according to claim 1, wherein the adjusting of the first jaw and the second jaw to the predetermined positions includes changing the positions of the first hole and the pin member with respect to the second hole in a state where the relative positions of the first hole and the pin member are fixed.

* * * * *